(12) United States Patent
Schuerch

(10) Patent No.: US 8,302,921 B2
(45) Date of Patent: Nov. 6, 2012

(54) SURGICAL APPLIANCE POST CLAMP FOR SURGICAL TABLES

(76) Inventor: Peter Schuerch, Quincy, MA (US)

(*) Notice: Subject to any disclaimer, the term of this patent is extended or adjusted under 35 U.S.C. 154(b) by 0 days.

(21) Appl. No.: 12/800,677

(22) Filed: May 21, 2010

(65) Prior Publication Data

US 2010/0230567 A1 Sep. 16, 2010

Related U.S. Application Data

(62) Division of application No. 11/398,934, filed on Apr. 6, 2006, now Pat. No. 7,731,141.

(60) Provisional application No. 60/668,551, filed on Apr. 6, 2005.

(51) Int. Cl.
*A47B 96/06* (2006.01)
*A47G 29/00* (2006.01)
*A47K 1/00* (2006.01)
*E04G 5/06* (2006.01)
*F21V 21/00* (2006.01)

(52) U.S. Cl. ............... 248/214; 248/218.4; 248/229.11; 248/286.1

(58) Field of Classification Search ............... 248/286.1, 248/218.4, 229.11, 214
See application file for complete search history.

(56) References Cited

U.S. PATENT DOCUMENTS

| | | | | |
|---|---|---|---|---|
| 4,547,092 A * | 10/1985 | Vetter et al. | | 403/59 |
| 5,538,215 A * | 7/1996 | Hosey | | 248/286.1 |
| 6,315,260 B1 * | 11/2001 | Lees | | 248/286.1 |
| 6,622,980 B2 * | 9/2003 | Boucher et al. | | 248/231.51 |
| 7,857,271 B2 * | 12/2010 | Lees | | 248/286.1 |

* cited by examiner

*Primary Examiner* — Amy J Sterling
(74) *Attorney, Agent, or Firm* — John M. Brandt

(57) ABSTRACT

A clamp for securing a surgical appliance post to a rail mounted on the side of a surgical table which clamp may be placed over and on the rail at any desired location by providing the clamp body with a passageway transverse the body of the clamp and parallel to the rail, the passageway having a lip on one edge of a width about the dimension of the rail for engaging the backside of the rail, and the passageway having a width greater than the rail on the opposite edge. A clamping device such as a screw or cam is mounted on the outermost portion of the clamp and is arranged to engage and secure the post as well as bind the clamp body to the rail. Additionally, the clamping arrangement of one of the preferred embodiments provides a means by which an appliance post may be gripped at any chosen angle rather than limited to a fixed orientation.

2 Claims, 4 Drawing Sheets

SURGICAL APPLIANCE POST CLAMP FOR SURGICAL TABLES

CROSS-REFERENCE TO RELATED APPLICATIONS

This application is based on the disclosure of Provisional Application Ser. No. 60/668,551 filed Apr. 6, 2005 by the same inventor which is hereby incorporated by reference and is a division of application Ser. No. 11/398,934 filed Apr. 6, 2006 now U.S. Pat. No. 7,731,141.

BACKGROUND OF THE INVENTION

1. Field of the Invention

The invention resides in the field of clamping devices for apparatus used in conjunction with surgical tables for medical operations.

2. Description of the Prior Art

Surgical tables for medical operations are almost universally equipped with a rail disposed about their edges to which may be affixed a post holding clamp. The rails are spaced apart from the table edge a standard distance and are of uniform dimension. The prior art clamps used with these rails have a channel oriented to the longitudinal axis of the rail which channel is slightly larger than the rail to allow the clamp to be slid along and positioned on the rail at a desired location. Gaps are provided in the rail to allow the clamp to be put on and taken off the rail as the need arises. The present invention eliminates the need for such gaps by providing, in the clamp body, a rail engaging passageway of different dimensions on each edge allowing the clamp to be placed on the rail at any desired location.

SUMMARY OF THE INVENTION

The invention may be summarized as an operating table clamp attachable to a side rail mounted on such tables for the purpose of securing surgical appliances in position during a surgical procedure. Such appliances are, among other devices, immobilizing supports or rests for body components and must be held in a secure and rigid manner. Posts of a standardize size and configuration are attached to the appliances to provide the means for mounting to the rail. Previously, clamps for joining the posts and rail had a passageway in the clamp body for receiving the rail which required gaps in the rail in order to slide the clamp on the rail. Alternatively, clamp bodies hinged on one side to open the passageway have been employed with means to swing and lock the hinged portion in place.

The invention herein utilizes a clamp body with a rail receiving passageway having one edge the size of the rail and the opposite edge larger than the rail to allow that passageway edge of the clamp body to be placed over the rail and then swung into place against the rail. The entire clamp, the post and the rail are then locked together by a clamping device such as a bolt or cam.

Two separate embodiments are described below. The first has such a passageway transverse the clamp body. A post port perpendicular to the passageway is provided for receiving an apparatus post and a clamping member is used to bind the post, clamp, and rail. A second perpendicular rail port adjacent the post port will engage a rail in the same manner as an alternative to the post.

In the second embodiment, additional clamping members are added to form a clamping assembly which allows the appliance post to be positioned and gripped at any angle with respect to the table and rail. These consist for example in addition to a bolt as above, a rotatable drum, and a clamp body extension, each with a co-alignable port for receiving the post, and a rail engaging extension. The various parts or clamping members fit together in a unique way to form the total clamping assembly to accomplish the purpose of the invention.

These and other features and advantages of the invention will be more fully understood from the description of the preferred embodiments taken with the drawings which follows.

DESCRIPTION OF THE PREFERRED EMBODIMENT

Figure 1:
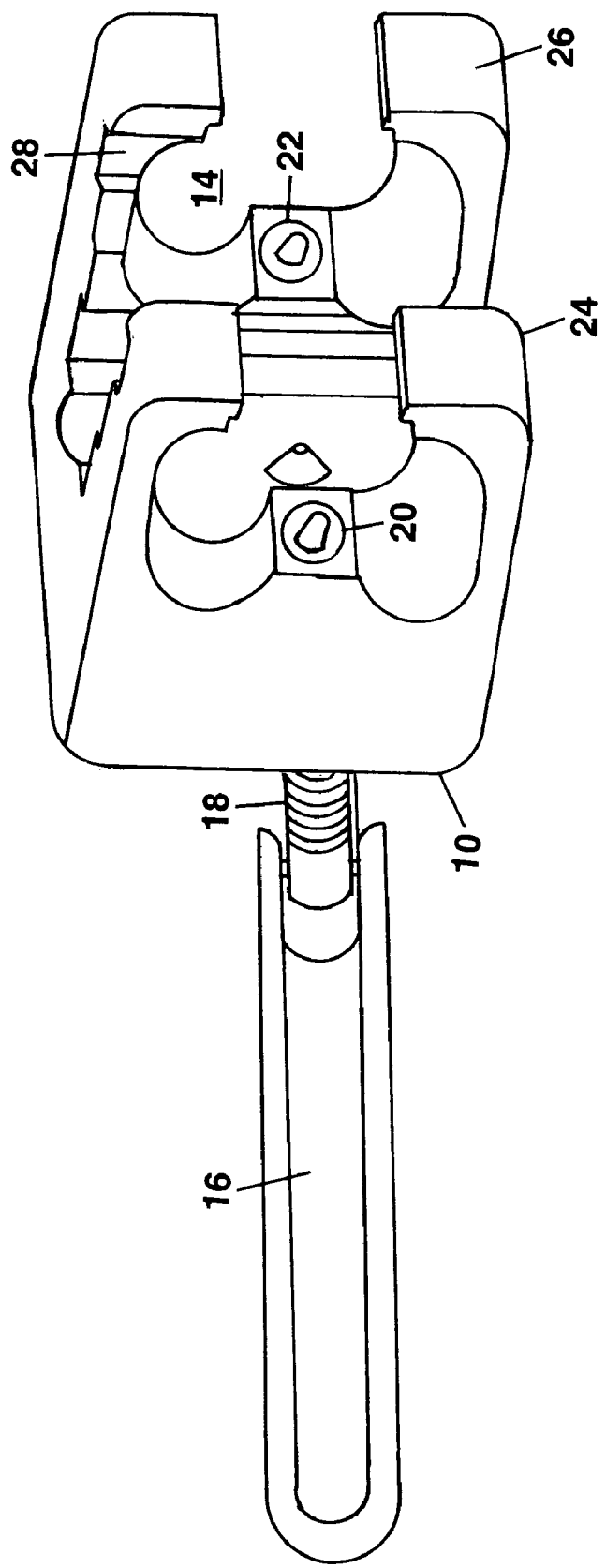
FIG. 1 is a perspective view of a first preferred embodiment of the invention.

Referring first to FIG. 1, there is shown a perspective illustration of a first preferred embodiment of the invention consisting of a clamp body 10 having surgical table rail receiving passage 12, post receiving port 14, clamping handle 16 operating clamping bolt 18, and rail spring biasing members 20 and 22 Post receiving port. 14 divides the first portion of body 12 into two spaced apart rail gripping extensions 24 and 26. Adjacent to and communicating with port 14 is a second port 28 sized to receive a length of surgical table rail.

Figure 2:
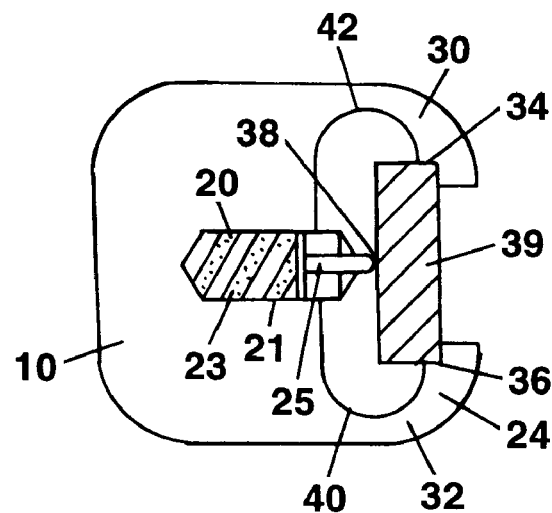
FIG. 2 is a cross-sectional side view of the embodiment of FIG. 1.

FIG. 2 is a cross-sectional side view of the clamp of FIG. 1 through rail gripping extension 24 and rail spring biasing member 20. As shown, both upper 30 and lower 32 front portions of extension 24 have lips 34 and 36 respectively, which, in conjunction with the tip 38 of spring biasing member 20, form an edge the size of rail 39. The edges 40 and 42 opposite the lip edges are larger than the width of the rail.

Figure 3:
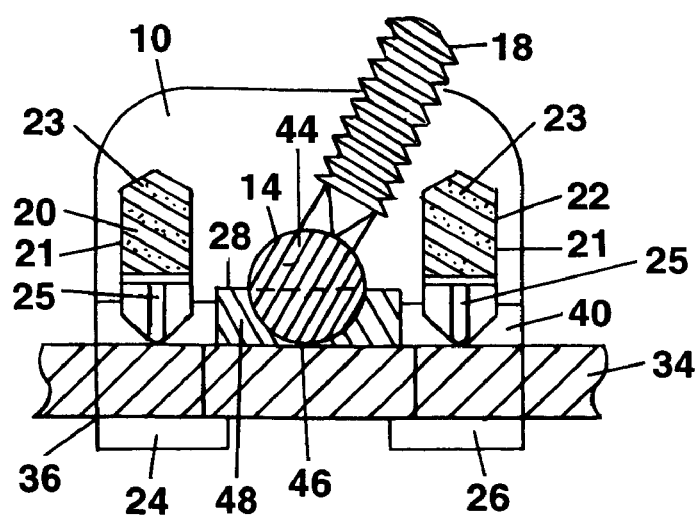
FIG. 3 is a cross-sectional top view of the embodiment of FIG. 1.

As further shown in FIG. 2, spring biasing member 20 consists of a well 21 disposed in clamp body 10, a spring 23 disposed in well 21, and a spring follower or plunger 25 terminating in tip 38 also disposed in well 21 forward of spring 23. As shown in FIG. 3, spring biasing member 22 is of the same construction as that of member 20.

FIG. 3 is a cross-sectional top view of FIG. 1 illustrating the manner in which clamp 10, rail 38, and post 44 are bound together by the force of bolt 18 as it is turned toward rail 39 by handle 16. Clamp body 10 is drawn outward from rail 39 while post 44 is forced against the rail at contact point 46. Alternatively, a rail 48 of the same dimension as the table rail for attaching surgical appliances may be vertically disposed in port 28, it being understood that either post 44 or rail 48 may be employed during a surgical procedure but not both at the same time.

Figure 4:
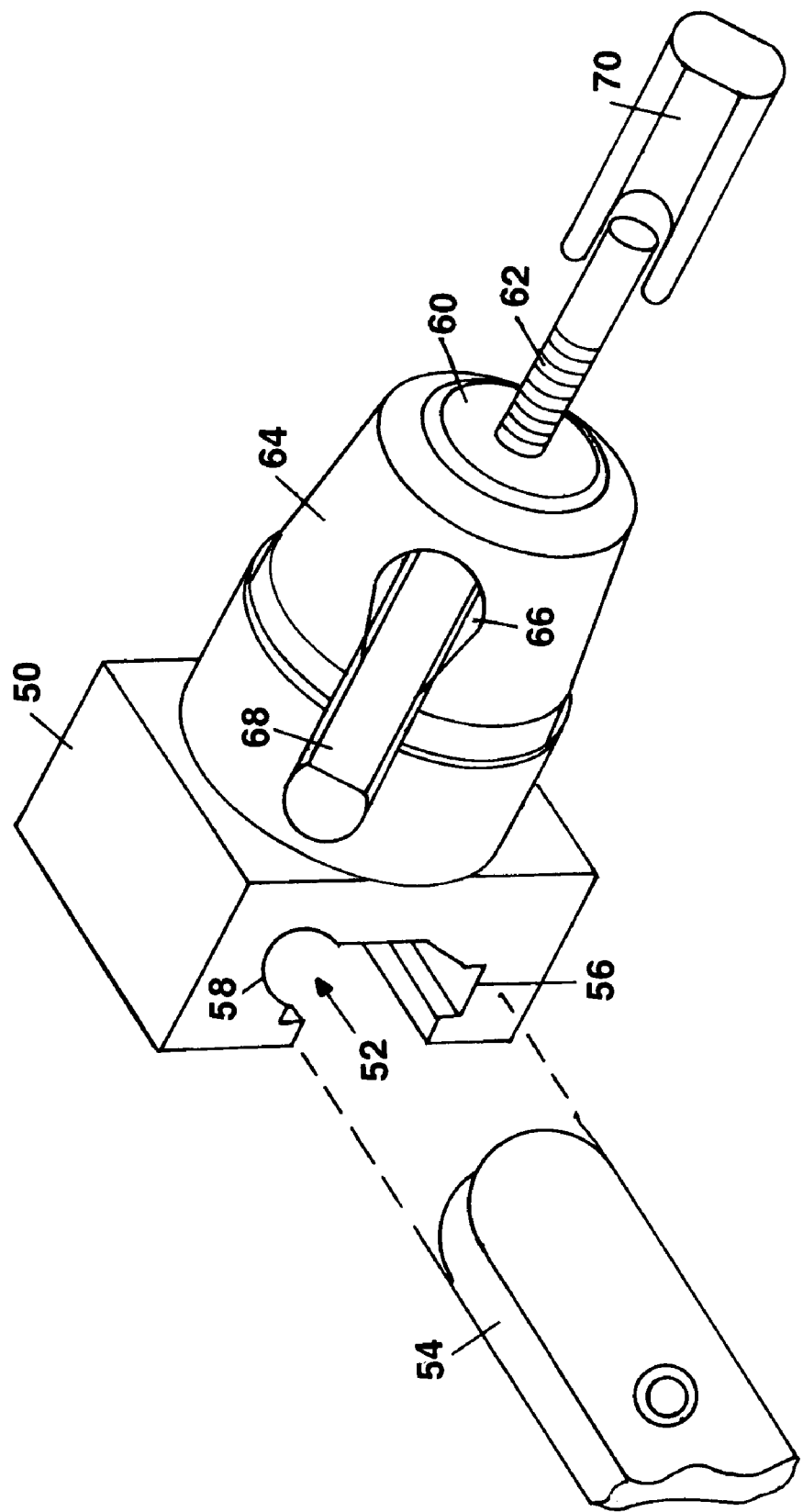
FIG. 4 is a perspective view of another preferred embodiment of the invention.

Referring next to FIG. 4, a perspective view of a second preferred embodiment of the invention is shown which provides for positioning the post at any desired angle with relation to the table rail. Clamp body 50 has passageway 52 extending completely across the length of the body for receiving surgical table rail 54. Passageway 52 is about the width of the rail along side 56 and greater than the rail along side 58.

Clamping members 60, 62, and 64 form a clamping assembly which will be further illustrated and described below. The assembly has port 66 consisting of co-aligning ports in members 64 and 60 for receiving a surgical appliance post 68. Handle 70, when rotated, will draw clamp members 62 and 64 together securing post 68 between clamp members 62 and 64, and forcing clamp member 64 against rail 54 to bind the entire combination of rail post and clamp.

Figure 5:
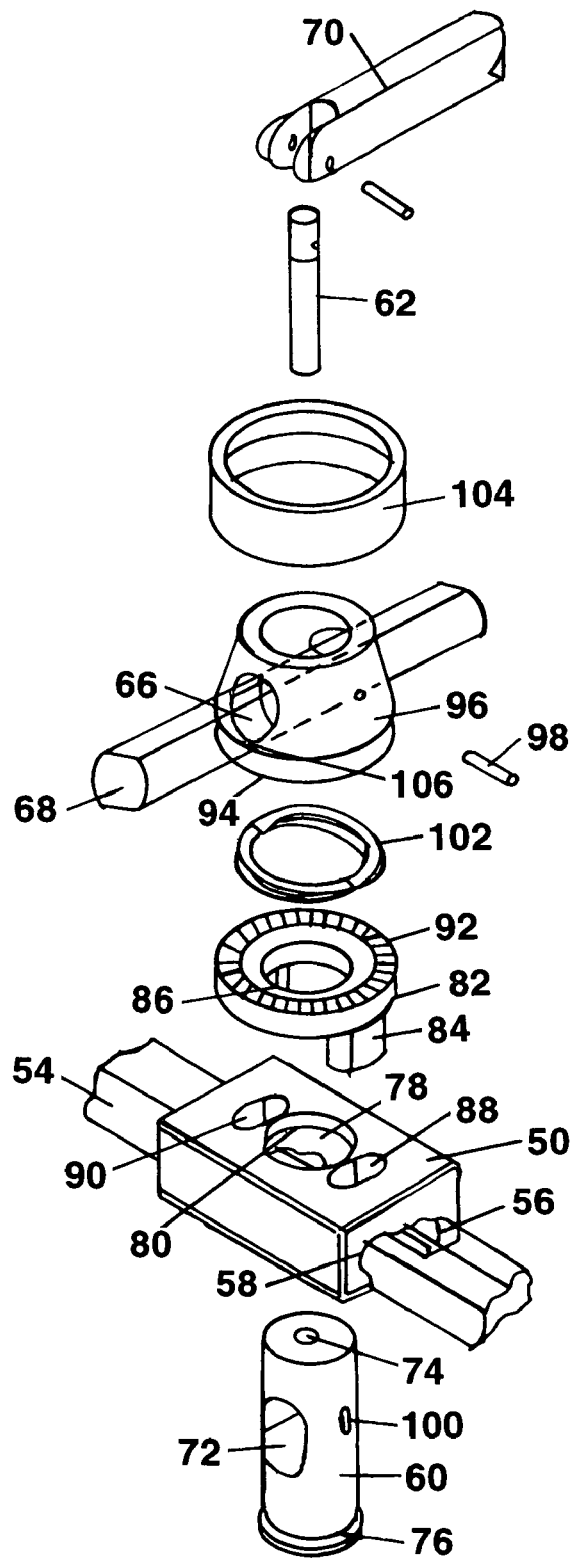
FIG. 5 is a broken out perspective view of the embodiment of FIG. 4.

FIG. 5 illustrates the components of the clamp of FIG. 4 broken out to show the interaction of the constituent parts. Clamp member 60 consists of a cylinder having post receiving port 72 and a threaded hole 74 for receiving clamp member 62, a bolt for example. The bottom of the cylinder is expanded into a lip 76. Clamp member 60 fits inside clamp body 50 extending upwards through port 78 and is limited in travel by lip 76 secured against the under topside 80 of clamp body 50.

Clamp member 64 consists of two parts. The first is a ring 82 having downward extending rail engaging members 84 and 86 which fit through ports 88 and 90 in body 50 to contact and bind rail 54 when the entire clamp system is compressed. The top 92 of ring 82 is serrated to engage the opposing serrations 94 formed on the bottom of body portion 96 forming the second part of clamp member 64. Body portion 96 has post-receiving port 66 which aligns with port 72 in clamp member 60 and is secured in position by pin 98 fitting into slot 100. Slot 100 has sufficient height to allow clamp member 64 parts 82 and 96 to slightly separate to allow body portion 96 to rotate free of the engagement of the serrations as described above.

Compressible spring 102 fits between ring 82 and body portion 96 to provide lateral tension. Guide ring 104 fits over ring 82 and the lower part of body portion 96 to provide alignment and secure spring 102.

In operation, clamp member or bolt 62 is rotated by handle 70 into hole 74 in clamp member 60 drawing the two parts together. This forces lip 76 of clamp member 60 against the underside 80 of clamp body 50 and binds post 68 against the lower surface 106 of port 66 in clamp member 64. As will be seen, when ring 82 and body portion 96 are separated, body portion 96, clamp member 64 and post 68 are free to rotate to orient the post. When these components are drawn together by the rotation of bolt 62 into clamp member 60, the opposing serrations 92 and 94 mate to secure the post in place at the desired angle.

As variations in the above described embodiments will now be apparent to those skilled in the art, the invention is accordingly defined by the following claims.

What is claimed is:

1. A clamp for securing a post equipped surgical appliance to a rail attached to a surgical operating table comprising in combination:
   A. a one piece clamp body for engaging said rail, said body having a pair of opposed spaced apart upper and lower clamp jaws for gripping said rail, said jaws arranged in fixed in place relationship to each other said body having a uniform profile passageway transverse said body and positioned between said jaws for receiving said rail, said passageway having a first and second portion, said first portion bounded by:
      1. a first side comprising a lip substantially equal to the width of said rail;
      2. a second side substantially perpendicular to said first side and substantially equal to the height of said rail; and
      3. a third side opposite said first side having a portion substantially perpendicular to said second side;
      said second portion communicating with said first portion for receiving said rail, said second portion disposed at the intersection of said second and third sides whereby said third side has a width greater than said rail to allow said clamp body to be placed over and against said rail from either longitudinal edge of said rail;
   B. a first clamp member extending outwardly from and arranged to engage said clamp body, said first clamp member having a transverse port for receiving said post;
   C. a second clamp member arranged to engage said first clamp member;
   D. a third clamp member disposed between said first and second clamp members extending through said clamp body for engaging said rail, said third clamp member having a transverse port for receiving said post coincident with said first clamp member transverse port; and
   E. means to draw said first and second clamp members together whereby said post is secured between said first and third clamp members and said third clamp member is secured against said rail.

2. A clamp for securing a post equipped surgical appliance to a rail attached to a surgical operating table comprising in combination:
   A. a one piece clamp body for engaging said rail, said body comprising a first rail gripping jaw, a second rail gripping jaw in spaced apart fixed in place relationship to said first jaw, and connecting means for attaching said jaws one to the other; said body having a uniform profile passageway transverse said body for receiving said rail, said passageway bounded by said jaws and said connecting means, said passageway having a first and second portion, said first portion defined by:
      1. a first side comprising a lip substantially equal to the width of said rail;
      2. a second side substantially perpendicular to said first side and substantially equal to the height of said rail; and
      3. a third side opposite said first side having a portion substantially perpendicular to said second side;
      said second portion communicating with said first portion for receiving said rail, said second portion disposed at the intersection of said second and third sides whereby said third side has a width greater than said rail to allow said clamp body to be placed over and against said rail from either longitudinal edge of said rail;
   B. a first clamp member extending outwardly from and arranged to engage said clamp body, said first clamp member having a transverse port for receiving said post;
   C. a second clamp member arranged to engage said first clamp member;
   D. a third clamp member disposed between said first and second clamp members extending through said clamp body for engaging said rail, said third clamp member having a transverse port for receiving said post coincident with said first clamp member transverse port; and
   E. means to draw said first and second clamp members together whereby said post is secured between said first and third clamp members and said third clamp member is secured against said rail.

* * * * *